United States Patent [19]

Lawton

[11] 3,972,933

[45] Aug. 3, 1976

[54] PREPARATION OF CARBODIIMIDES FROM UREAS BY DEHYDRATION

[75] Inventor: Ernest L. Lawton, Durham, N.C.

[73] Assignee: Monsanto Company, St. Louis, Mo.

[22] Filed: May 28, 1974

[21] Appl. No.: 473,616

[52] U.S. Cl. ............................................ 260/566 R
[51] Int. Cl.² .................................... C07C 119/00
[58] Field of Search ................. 260/566 R, 551 CD

[56] References Cited
OTHER PUBLICATIONS

Smith, "Open Chain Nitrogen Compounds," vol., pp. 257–258, (1965).

Primary Examiner—Gerald A. Schwartz
Attorney, Agent, or Firm—Robert L. Broad, Jr.

[57] ABSTRACT

Biscarbodiimides which are known to be effective as a surface application for polyethylene terephthalate fibers in lowering carboxyl end group concentration of the fibers and increasing hydrolytic stability, are prepared by the dehydration of ureas with triphenylphosphine and carbon tetrachloride.

5 Claims, No Drawings

PREPARATION OF CARBODIIMIDES FROM UREAS BY DEHYDRATION

BACKGROUND OF THE INVENTION

Synthetic linear polyester filaments, yarns and cords are known to show improved strength under hydrolytic conditions or elevated temperatures when, either by the use of certain additives to the polymer, or chemical coatings on the polyester fiber, the carboxyl end group concentration is lowered.

One of the commonly employed methods of lowering the carboxyl level is by applying to the polyester fiber a surface coating which consists essentially of a carbodiimide or polycarbodiimide. United States patents relating to the use of such carbodiimides or polycarbodiimides include U.S. Pat. No. 3,193,523, U.S. Pat. No. 3,193,524, and U.S. patent application Ser. No. 302,710 filed Nov. 1, 1972.

SUMMARY OF THE INVENTION

It is an object of this invention to provide a new and improved method of preparing biscarbodiimides.

Briefly, the object of this invention is attained by dehydration of ureas by triphenylphosphine and carbon tetrachloride reactants according to the reaction sequence shown in the following typical example:

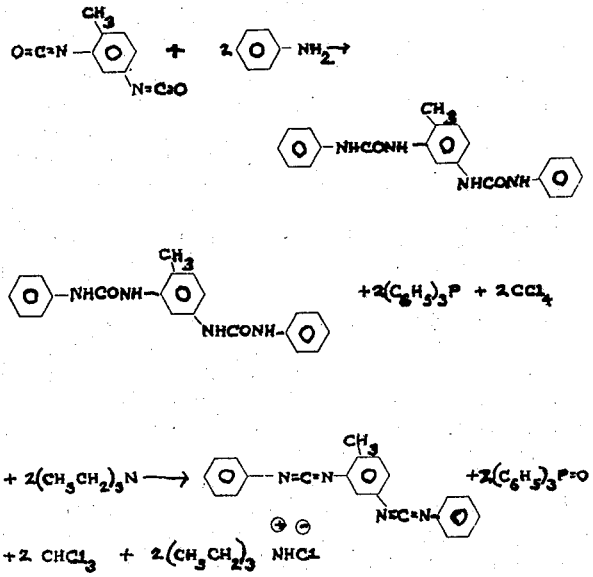

DESCRIPTION OF THE PREFERRED EMBODIMENTS

The reactants are rather common and relatively inexpensive and the products are substantially free of residual isocyanates and uretidinedione imines.

Separation and isolation of the carbodiimide from the triphenylphosphine oxide was sometimes difficult, and has been demonstrated by vacuum distillation although fractional crystallization and extraction may well be practical.

In the production of certain biscarbodiimides, it was recognized that the product being isolated was a monocarbodiimide of the terminal groupings (R' and R'') of the bisurea rather than the desired biscarbodiimide. The possibility of inter- or intramolecular rearrangement of a reaction intermediate during dehydration is considered a possible explanation.

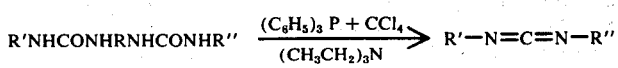

+ other products

Another possibility is that intra- or intermolecular rearrangement of the desired biscarbodiimide occurred during isolation of the reaction products.

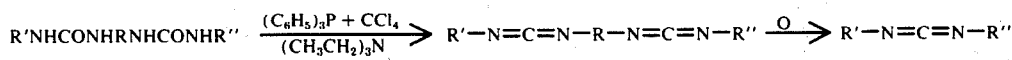

+ other products

The separation of the biscarbodiimides from other products by distillation, for example, resulted in rearrangement in accordance with the following equation:

where

| R | R' |
|---|---|
| CH$_3$(CH$_2$)$_5$— | CH$_3$ —⟨O⟩— |
|  | CH$_3$ —⟨O⟩— |
| ⟨O⟩— | CH$_3$ —⟨O⟩— |
| ⟨O⟩— | —⟨O⟩— |
| ⟨O⟩— | —(CH$_2$)$_6$— |

Notwithstanding problems of rearrangement, biscarbodiimides which are effective as additives for polyethylene terephthalate tire yarn as stabilizers against hydrolytic degradation can be prepared in good yield by this dehydration method.

The following examples should not be construed to limit the scope of this invention.

EXAMPLE 1

Preparation of Bis (N, N'-Ureas)

The amine (0.41 mole) dissolved in 200 ml of tetrahydrofuran was placed in a 1000-ml flask equipped with a mechanical stirrer, dropping funnel, and nitrogen inlet to maintain an atmosphere of nitrogen above the reactants. The flask was cooled by an ice bath. The diisocyanate (0.20 mole) dissolved in 200 ml of tetrahydrofuran was dropped into the amine solution over a 2-hr period. Upon completion of the addition, stirring was continued for 12 hr at room temperature.

EXAMPLE 2

Preparation of [Bis-1, 1'-Phenyl] - [3,3 - (Tolylene-2,4)]Diurea

The diurea was prepared from aniline (Eastman, MP −6 to −5°) and tolylene-2,4-diisocyanate (Fisher, practical). At conclusion of the 14-hr reaction period, a white precipitate had formed. The precipitate was isolated by filtration and washed with water. The material was then slurried with 2 l of 2 N aqueous hydrochloric acid in a blender, filtered, slurried three times with 2 l portions of water and filtered, and then rinsed with acetone. After drying at 110°C under 20 mm Hg pressure for 12 hr, a white powder was obtained.

EXAMPLE 3

Preparation of [Bis-1,1'-Phenyl] - [3,3'-(Phenylene-1,4]Diurea

The diurea was prepared from phenyl isocyanate (Fisher, BP 55°–56°/13mm) and p-phenylene diamine (Fisher, certified). The isocyanate was dropped into the diamine solution. At conclusion of the 14-hr reaction period, a grey precipitate had formed. The precipitate was isolated by filtration and washed with water. The material was then slurried with 2 l of 2 N aqueous hydrochloric acid in a blender, filtered, slurried three times with 2 l portions of water and filtered, and then rinsed with acetone. After drying at 110° C under 20 mm Hg pressure for 12 hr, a grey powder was obtained.

EXAMPLE 4

Preparation of [Bis-1, 1'-n-Hexyl] - [3,3' - (Tolylene-2,4 )] Diurea

The diurea was prepared from n-hexyl amine (Eastman, BP 128°–130°) and tolylene-2,4diisocyanate (Fisher, practical). At conclusion of 14-hr reaction period, a white precipitate had formed. The precipitate was isolated by filtration and washed with acetone. The material was recrystallized from ethanol/chloroform.

EXAMPLE 5

Preparation of [Bis-1,1'-Phenyl] - [3,3' - Hexamethylene]Diurea

The diurea was prepared from aniline (Eastman, MP −6° to −5°) and hexamethylene diisocyanate (Eastman, MP 40°–42°). At conclusion of 14-hr reaction period, a white precipitate had formed. The precipitate was isolated by filtration and washed with acetone. The material was recrystallized from dimethylsulfoxide/acetone.

EXAMPLE 6A

Dehydration of

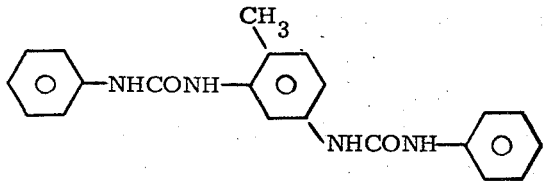

The urea (0.050 mole), triethylamine (0.100 mole) were added to 100 ml of dichloromethane in a round bottom flask equipped with a mechanical stirrer and condenser. The dichloromethane was refluxed at approximately 40° C for 5 hr. During the first hour of refluxing, a yellow solution was obtained. Precipitation of triethylamine hydrochloride occurred after several hours at reflux. The reaction mixture was cooled to room temperature, filtered, and the residue washed with dichloromethane. The filtrate was washed twice with 200-ml portions of water. The dichloromethane layer was dried over magnesium sulfate, filtered, and then evaporated to dryness at room temperature under 1 mm Hg pressure using a rotatory vacuum apparatus. This residue was then vacuum distilled. An Ace Glass mini-vacuum distillation head with a 15-cm Vigreux column was used.

A clear liquid boiling at 123°–126°C (0.5 mm Hg) was obtained. Infrared and mass spectra indicated that the compound obtained was N,N'-diphenylcarbodiimide instead of the expected biscarbodiimide. Elemental analysis was consistent with $C_{13}H_{10}N_2$ rather than $C_{21}H_{16}N_4$; calculated 80.38%C, 5.19%H, 14.43%N; found: 78.91%C, 5.23%H, 14.00%N. The nuclear magnetic resonance spectrum of the compound in $CDCl_3$ exhibited only a multiplet at 7.15 to 7.45δ (ppm). The infrared spectrum of the compound was identical to that of $C_6H_5$—N=C=N—$C_6H_5$. The mass spectral cracking pattern of the compound also appeared equivalent to that of $C_6H_5$—N=C=N—$C_6H_5$. The yield was 45% of theory.

The white precipitate which formed during the dehydration was isolated by filtration, washed with dichloromethane, and dried at 80° C under 20 mm Hg pressure. The precipitate weighed 1.5 g and was identified as triethylamine hydrochloride by comparison of its infrared and nuclear magnetic resonance spectra with those of an authentic sample. The water washes used to remove the amine hydrochloride from the dichloromethane reaction solution were evaporated to dryness to yield 12.3 g of residue with infrared (KBr pellet) and nuclear magnetic resonance ($D_2O$ solution) spectra identical to those of triethylamine hydrochloride.

A 10-ml portion of the dichloromethane reaction solution was washed with $D_2O$ and the nuclear magnetic resonance spectrum of the $D_2O$ wash was then obtained. The spectrum indicated the presence of only triethylamine hydrochloride with no signals in the 7 to 9δ region indicative of phenyl protons.

A 10-ml portion of the water-washed dichloromethane reaction solution was evaporated to dryness under a nitrogen sweep at room temperature, and the nuclear magnetic resonance spectrum of the residue was determined in $CDCl_3$. The spectrum exhibited phenyl proton signals at 7 to 8δ and an aryl $CH_3$ signal at 2.3δ ; the spectrum did not exhibit a NH signal in the 8 to 9δ region. The nuclear magnetic resonance spectrum thus incicated the presence of the desired biscarbodiimide in the dichloromethane reaction solution. The infrared spectrum of this residue exhibited absorptions attributable to triphenylphosphine oxide and a strong carbodiimide absorption at 2140 cm$^{-1}$ but only slight if any amide absorptions at 3200 cm$^{-1}$, 1650 cm$^{-1}$, or 1550 cm$^{-1}$ were observed.

The pot residue after distillation of the reaction products consisted of triphenylphosphine oxide and residual aryl carbodiimides as evidenced by the infrared spectrum of the residue. The spectrum consisted of the characteristic absorptions of triphenylphosphine oxide at 1430, 1180, 1120, 995, 755, 720, and 695 cm$^{-1}$; and the carbodiimide absorption at 2150 cm$^{-1}$. No absorptions in the 1600 to 1700 cm$^{-1}$ region were exhibited, thus indicating no dimers, trimers or polymers derived from the reaction of carbodiimide groups to yield

groups.

EXAMPLE 6B

The dehydration was repeated as described above except that the separation of the products was varied in an attempt to isolate the biscarbodiimide The alternate procedure was employed to verify the rearrangement theory. In this procedure, the filtered dichloromethane reaction solution was evaporated to dryness under 20 mm Hg pressure at room temperature. The residue was then extracted with petroleum ether (38°–51°) for 3 hrs. in a Soxhlet apparatus. The petroleum ether was removed under vacuum to yield 10.1 g of petroleum ether soluble residue, a 60% yield of the crude biscarbodiimide based upon the equation. The nuclear magnetic resonance spectrum of the residue in CDCl$_3$ exhibited a multiplet from phenyl protons at 7.1 to 7.7δ and a singlet from the aryl CH$_3$ protons at 2.30δ (ppm). The relative area of the two signals was (phenyl H) / (CH$_3$) = 4.5. The mass spectrum exhibited the molecular ion at (m/e) of 324 for the biscarbodiimide

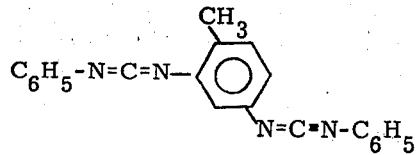

and the cracking pattern was consistent with this structure.

Elemental analysis for the petroleum ether soluble material was 77.19% C, 5.02% H, and 14.37% N. The calculated values for C$_{21}$H$_{16}$N$_4$ are 77.75%C, 4.97%H, and 17.28%N.

Apparently the dehydration reaction yields the expected biscarbodiimide, but this compound rearranges during distillation to yield N,N'-diphenylcarbodiimide as a product.

The petroleum ether soluble residue was vacuum distilled to yield 3.5 g of clear liquid boiling at 160°–170°C (0.35 mm Hg). The yield of N,N'-diphenylcarbodiimide was 36% of theory. The infrared spectrum appears identical with that of N,N'-diphenylcarbodiimide. The mass spectrum cracking pattern appears equivalent to that of diphenylcarbodiimide. The nuclear magnetic resonance spectrum in CDCl$_3$ exhibited only a multiplet at 7.1 to 7.4δ(ppm). Elemental analysis was satisfactory for C$_{13}$H$_{10}$N$_2$; calculated: 80.38%C, 5.19%H, 14.43%N; found: 79.75%C, 5.10%H, 13.98%N.

The dehydration was repeated; and after filtration, the dichloromethane reaction solution was extracted with water and then dried over magnesium sulfate. The dichloromethane was removed, and the residue was extracted with petroleum ether. The petroleum ether solubles were isolated and distilled. Results of this separation were equivalent to those described above for the separation using an unwashed dichloromethane solution.

EXAMPLE 7

Dehydration of

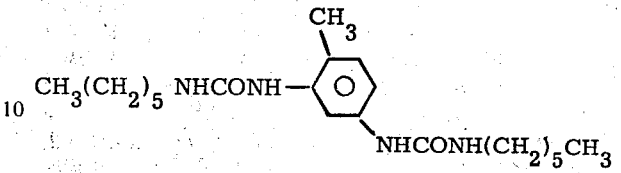

From distillation of the dichloromethane soluble products, the urea was dehydrated as described in Example 6A. A clear liquid boiling at 112°C (0.6 mm Hg) was obtained. Infrared and mass spectra indicated that the compound obtained was N,N'-di-n-hexylcarbodiimide instead of the expected biscarbodiimide. Elemental analysis was consistent with C$_{13}$H$_{26}$N$_2$ rather than C$_{21}$H$_{32}$N$_4$; calculated:74.22%C, 12.46%H, 13.32%N; found: 73.2%C, 10.95%H, 13.53%N. The nuclear magnetic resonance spectrum of the compound in CDCl$_3$ exhibited the following signals:

| δ(ppm) | | Relative area |
|---|---|---|
| 0.95 (triplet, J$_{HH}$ = 6, CH$_3$) | $\frac{CH_3}{CH_2N}$ | ≈ 1.2 |
| 1.20 – 1.70 (multiplet, [CH$_2$]$_4$) | | |
| 3.25 (triplet, J$_{HH}$ = 7, —CH$_2$N—) | $\frac{[CH_2]_4}{-CH_2N-}$ | ≈ 4.1 |

The infrared spectrum of the compound was identical with that of CH$_3$(CH$_2$)$_5$—N=C=N—(CH$_2$)$_5$CH$_3$. The mass spectral cracking pattern of the compound also appeared equivalent to that of CH$_3$(CH$_2$)$_5$—N=C=N—(CH$_2$)$_5$CH$_3$. The yield of CH$_3$(CH$_2$)$_5$—N=C=N—(CH$_2$)$_5$CH$_3$ was 51% of theory.

EXAMPLE 8

Dehydration of

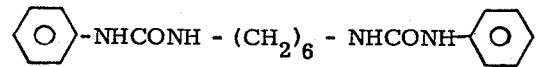

The urea was dehydrated as described in Example 6A. From distillation of the dichloromethane soluble products, a clear liquid boiling at 139°–143° C ( 0.2 mm Hg) was obtained. Infrared and mass spectra indicated that the compound obtained was N,N'-diphenylcarbodiimide instead of the expected biscarbodiimide. Elemental analysis was consistent with C$_{13}$H$_{10}$N$_2$ rather than C$_{20}$H$_{22}$N$_4$; calculated: 80.38%C, 5.19%H, 14.43%N found: 80.05%C, 5.55%H, 13.80%N. The nuclear magnetic resonance spectrum of the compound in CDCl$_3$ exhibited only a multiplet at 7.0 – 7.4δ (ppm). The infrared spectrum of the compound appeared identical to that of C$_6$H$_5$—N=C=N—C$_6$H$_5$. The mass spectral cracking pattern of the compound also appeared equivalent to that of C$_6$H$_5$—N=C=N—C$_6$H$_5$. The yield was 56% of theory.

EXAMPLE 9

Dehydration of

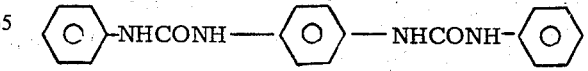

The urea was dehydrated as described in Example 6A. From distillation of the dichloromethane soluble products, a clear liquid boiling at 149° –151° C (1.1 mm Hg) was obtained. Infrared and mass spectra indicated that the compound obtained was N,N'-diphenylcarbodiimide instead of the expected biscarbodiimide. Elemental analysis was consistent with $C_{13}H_{10}N_2$ rather than $C_{20}H_{14}N_4$; calculated: 80.38%C, 5.19%H, 14.43%N; found 79.63%C, 5.47%H, 13.97%N. The nuclear magnetic resonance spectrum of the compound in $CDCl_3$ exhibited only a multiplet at 7.0 to 7.4δ (ppm.) The infrared spectrum of the compound appeared identical to that of $C_6H_5$—N=C=N—$C_6H_5$. The mass spectral cracking pattern of the compound also appeared equivalent to that of $C_6H_5$—N=C=N—$C_6H_5$. The yield was 58% of theory.

I claim:

1. The method of producing biscarbodiimides by dehydrating bisureas with triethylamine, triphenylphosphine, and carbon tetrachloride.

2. The method of claim 1 wherein the bisurea is produced by dehydration of

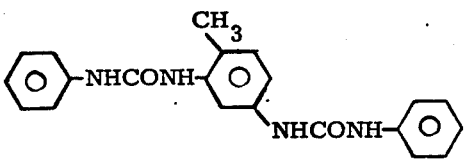

and the product is

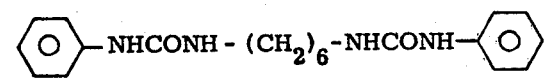

3. The method of claim 1 wherein the bisurea is produced by dehydration of

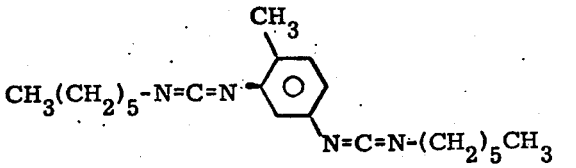

and the product is

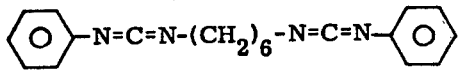

4. The method of claim 1 wherein the bisurea is produced by dehydration of

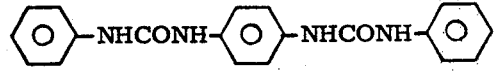

and the product is

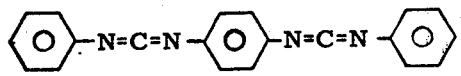

5. The method of claim 1 wherein the bisurea is produced by dehydration of

⟨O⟩-NHCONH-⟨O⟩-NHCONH-⟨O⟩ and the product is

⟨O⟩-N=C=N-⟨O⟩-N=C=N-⟨O⟩

* * * * *

UNITED STATES PATENT OFFICE
CERTIFICATE OF CORRECTION

PATENT NO. : 3,972,933
DATED : August 3, 1976
INVENTOR(S) : Ernest L. Lawton

It is certified that error appears in the above-identified patent and that said Letters Patent are hereby corrected as shown below:

Col. 1, line 28, reads "mides include U.S. Pat. No. 3,193,523, U.S. Pat. No.", should read:

---mides include U.S. Pat. No. 3,193,522, U.S. Pat. No. 3,193,523, U.S. Pat. No.---.

Col. 3, line 67, reads "The urea (0.50 mole), triethylamine (0.0100 mole)", should read:

---The urea (0.050 mole), triethylamine (0.100 mole), triphenylphosphine (0.120 mole), and a carbon tetrachloride (0.120 mole)---.

Signed and Sealed this

Eighth Day of March 1977

[SEAL]

Attest:

RUTH C. MASON
Attesting Officer

C. MARSHALL DANN
Commissioner of Patents and Trademarks